United States Patent
Krahbichler et al.

(10) Patent No.: US 6,345,538 B1
(45) Date of Patent: Feb. 12, 2002

(54) DUAL CHAMBER ULTRASONIC FLOW METER WITH MEMBRANES HAVING EQUAL PRESSURE ON OPPOSITE SIDES THEREOF

(75) Inventors: Erik Krahbichler, Straubing (DE); Lars Wallen, Spånga; Göran Skog, Bromma, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/292,614

(22) Filed: Apr. 15, 1999

(30) Foreign Application Priority Data

Apr. 23, 1998 (SE) .............................. 9801430

(51) Int. Cl.[7] .............................. G01F 1/66; A62B 23/00
(52) U.S. Cl. .................. 73/861.27; 128/205.14
(58) Field of Search ................ 73/861.25, 861.26, 73/861.27, 861.28, 861.18; 128/205.14, 204.18, 205.11

(56) References Cited

U.S. PATENT DOCUMENTS

| 4,173,889 A | | 11/1979 | Forester et al. |
| 4,321,835 A | * | 3/1982 | Martin .................. 73/861.28 |
| 4,581,942 A | | 4/1986 | Ogura et al. |
| 5,419,326 A | | 5/1995 | Harnoncourt |
| 5,645,071 A | * | 7/1997 | Harnocourt et al. ..... 73/861.28 |
| 5,647,370 A | | 7/1997 | Harnoncourt |
| 5,957,130 A | * | 9/1999 | Krahbichier et al. ... 128/205.14 |
| 6,058,786 A | * | 5/2000 | Wallen et al. .......... 73/861.28 |

FOREIGN PATENT DOCUMENTS

| DE | 19648784 A 1 | 11/1996 |
| EP | 0713711 A 2 | 10/1995 |

\* cited by examiner

Primary Examiner—Harshad Patel
(74) Attorney, Agent, or Firm—Schiff Hardin & Waite

(57) ABSTRACT

An ultrasonic flow meter for measuring a flow in a measurement channel has a first sensor chamber with a first membrane arranged against the measurement channel and a first transducer arranged at a specific distance from the first membrane, and a second sensor chamber with a second membrane arranged against the measurement channel and a second transducer arranged at a specific distance from the second membrane is described. The first membrane and the second membrane are gas-tight. In order to reduce loads on the membrane, while still allowing the membrane to be made as thin as possible, the first sensor chamber and the second sensor chamber are gas-tight, a first gas line connects the first sensor chamber to the measurement channel and a second gas line connects the second sensor chamber to the measurement channel.

5 Claims, 1 Drawing Sheet

DUAL CHAMBER ULTRASONIC FLOW METER WITH MEMBRANES HAVING EQUAL PRESSURE ON OPPOSITE SIDES THEREOF

BACKGROUND OF THE INVENTION

1. Field of the Invention

The present invention is directed to an ultrasonic flow meter of the type for determining a flow in a measurement channel, having a first sensor chamber with a first membrane disposed against the measurement channel and a first transducer disposed at a specific distance from the first membrane, and a second sensor chamber with a second membrane disposed against the measurement channel and a second transducer disposed at a specific distance from the second membrane, with the first and second membranes being gas-tight.

2. Description of the Prior Art

Ultrasonic flow meters are known in various areas of flow measurement, including the medical field in which the flow of gas expired by a patient is measured. The technique is well known and employs transducers that transmit sound waves between each other, with the transit time measured upstream and downstream serving as the basis for calculating the flow.

When a measurement is to be made in a sensitive environment or, in the case of medical applications, when contamination of the transducers must be avoided, a membrane is utilized between the transducers and the measurement channel.

These membranes can consist of porous filters with a bacteria-blocking capability, however, porous filters with a sufficient bacteria-blocking effect are too thick and have a damping effect on ultrasound. The membrane can instead be gas-tight for reliable prevention of contamination.

The membrane should also be as thin as possible, preferably less than 10 $\mu$m, in order to pass ultrasonic waves as effectively as possible. For such thin membranes, variations in pressure that could cause the membrane to rupture are then a risk.

Ideally, therefore, the membrane should be durable enough to withstand extended usage and resist rupturing.

SUMMARY OF THE INVENTION

An object of the present invention is to provide an ultrasonic flow meter that avoids the aforesaid problems.

The above object is achieved in accordance with the invention in an ultrasonic flow meter of the type initially described, wherein the first and second sensor chambers each are gas-tight, and wherein a first gas line connects the first sensor chamber to the measurement channel and a second gas line connects the second sensor chamber to the measurement channel.

Another object of the invention is to provide a ventilator in which the ultrasonic flow meter is incorporated.

This object is achieved in accordance with the invention in a ventilator which supplies a breathing gas to a patient via a gas line in which an ultrasonic flow meter is disposed for measuring the flow of the breathing gas, the ultrasonic flow meter being constructed in accordance with the invention as described immediately above.

When the sensor chambers are connected to the measurement channel, pressure equalization is achieved that minimizes the loading to which the membrane is subjected, and membranes can accordingly be made as thin as possible.

Filters should be arranged by the connections between the measurement channel and the sensor chambers in order to prevent contamination.

DESCRIPTION OF THE PREFERRED EMBODIMENTS

Figure 1:
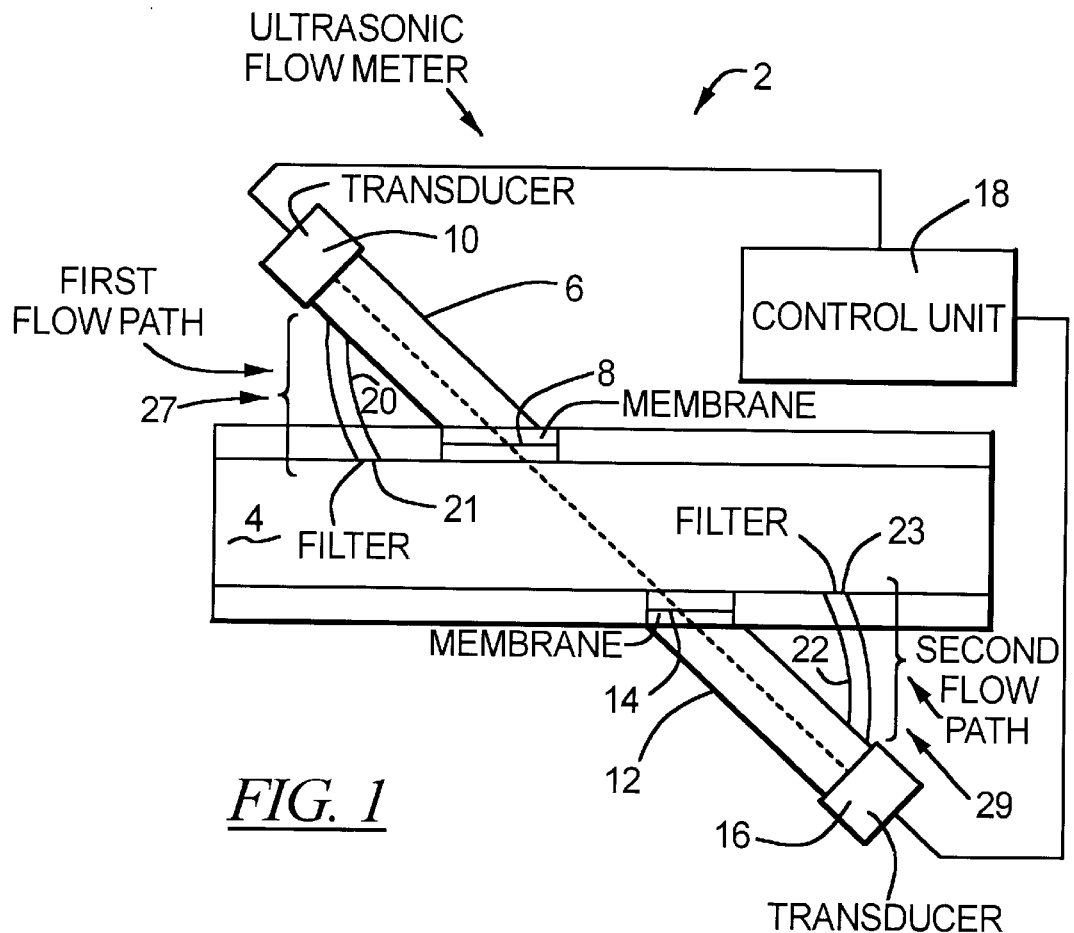
FIG. 1 shows a first embodiment of the ultrasonic flow meter according to the invention.

A first embodiment of the ultrasonic flow meter is shown in FIG. 1 and designated 2. The ultrasonic flow meter 2 is mounted by or contains a measurement channel 4 for the flow to be measured. A gas flow is preferably measured.

A first sensor chamber 6 is connected to the measurement channel 4 and is separated from it by a first membrane 8. The first membrane 8 is gas-tight to prevent the leakage of gas into the first sensor chamber 6. The first membrane 8 is made as thin as possible to keep it from obstructing sound waves to/from a first transducer 10 arranged in the first sensor chamber 6.

In a corresponding manner, a second sensor chamber 12 is connected to the measurement channel 4. The second sensor chamber 12 contains a second membrane 14 and a second transducer 16.

The signals from the transducers 10, 16 are supplied to a control unit 18 for the ultrasonic flow meter 2. The flow is determined in the control unit 18 in a manner known for this type of meter.

To prevent pressure variations in the measurement channel 4 from subjecting the first membrane 8 to excessive loading, a first gas line 20, which forms a part of a first flow path 27, is connected between the measurement channel 4 and the first sensor chamber 6. A first filter 21 in the first flow path 27 removes any contaminated constituents from the gas in the measurement channel 4 before the gas passes into the first sensor chamber 6.

As a result of the connection between the measurement channel 4 and the first sensor chamber 6, rapid equalization of pressure is achieved on both sides of the first membrane 8, thereby minimizing mechanical loading on the first membrane 8.

In a corresponding manner, a second gas line 22, which forms a part of a second flow path 29, connects the measurement channel 4 to the second sensor chamber 12 via a second filter 23 in the second flow path 29.

Except for the respective connections produced by the first gas line 20 and the second gas line 22, the sensor chambers 6 and 12 are gas-tight.

Figure 2:
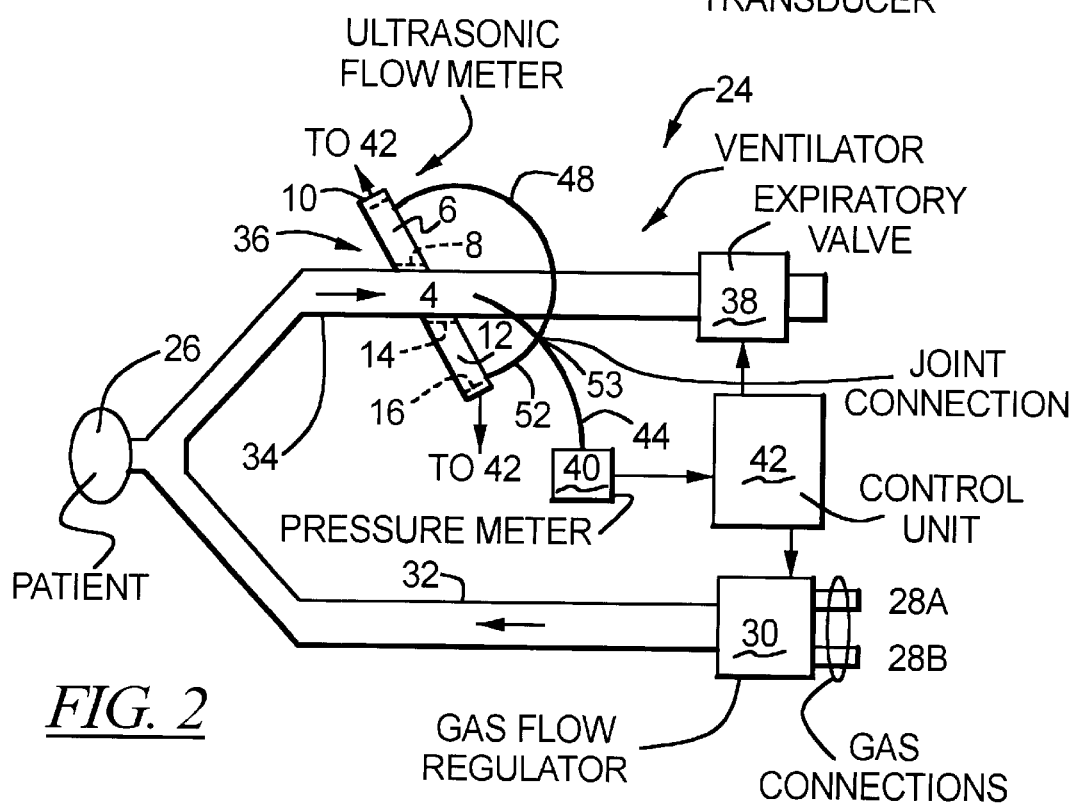
FIG. 2 shows a second embodiment of the ultrasonic flow meter according to the invention, installed in a ventilator.

FIG. 2 shows an advantageous practical application of the ultrasonic flow meter, according to the invention, in a ventilator 24. The ventilator 24 can be connected to a patient 26 to provide breathing assistance and contains (schematically depicted) a first gas connection 28A, a second gas connection 28B, a gas flow regulator 30, an inspiratory line 32, an expiratory line 34, an ultrasonic flow meter 36, an expiratory valve 38, a pressure meter 40 and a control unit 42.

The pressure meter 40 is connected to the expiratory line 34 by a measurement tube 44 for measuring expiratory pressure. The measurement tube 44 contains a bacterial filter (not shown) at the connection to the expiratory line 34 in the known manner.

The ultrasonic flow meter 36 is a second embodiment of the ultrasonic flow meter according to the invention. In this instance, the first sensor chamber 6 is connected at a joint connection 53 to the expiratory line 34 by a first gas line 48 and the measurement tube 44.

In a corresponding manner, the second sensor chamber 12 is connected to the expiratory line 34 by a second gas line 52 and the measurement tube 44.

The number of openings in the expiratory line 34 and the number of bacterial filters are thus reduced, compared to the situation if the ultrasonic flow meter 2 as shown in FIG. 1 were used in the ventilator 24.

Although modifications and changes may be suggested by those skilled in the art, it is the intention of the inventors to embody within the patent warranted hereon all changes and modifications as reasonably and properly come within the scope of their contribution to the art.

We claim as our invention:

1. An ultrasonic flow meter comprising:
   a measurement channel in which a fluid flow is measured;
   a first sensor chamber having a membrane disposed gas-tight against said measurement channel;
   a transducer disposed in said first sensor chamber at a predetermined distance from said membrane in said first chamber;
   a second sensor chamber having a membrane disposed gas-tight against said measurement channel;
   a transducer disposed in said second sensor chamber at a predetermined distance from said membrane in said second sensor chamber;
   a first gas line placing said first sensor chamber in fluid communication with said measurement channel and said first sensor chamber being otherwise gas-tight;
   a second gas line placing said second sensor chamber in fluid communication with said measurement channel and said second sensor chamber being otherwise gas-tight; and
   a control unit connected to said transducer in said first sensor chamber and to said transducer in said second sensor chamber for operating said transducers to transmit and receive ultrasound therebetween, said ultrasound having a transit time between said transducers, and for measuring said fluid flow dependent on said transit time.

2. An ultrasonic flow meter as claimed in claim 1 further comprising a joint connection connecting said first gas line and said second gas line to said measurement channel.

3. An ultrasonic flow meter as claimed in claim 1 further comprising a first flow path including said first gas line between said measurement channel and said first sensor chamber, a second flow path including said second gas line between said measurement channel and said second sensor chamber, and a filter disposed in said first flow path, and a filter disposed in said second flow path.

4. A ventilator comprising:
   a regulator supplying breathing gas;
   an ultrasonic flow meter in fluid communication with said regulator, said ultrasonic flow meter comprising:
      a measurement channel through which said breathing gas flows at a fluid flow;
      a first sensor chamber having a membrane disposed gas-tight against said measurement channel;
      a transducer disposed in said first sensor chamber at a predetermined distance from said membrane in said first sensor chamber;
      a second sensor chamber having a membrane disposed gas-tight against said measurement channel;
      a transducer disposed in said second sensor chamber at a predetermined distance from said membrane in said second sensor chamber;
      a first gas line placing said first sensor chamber in fluid communication with said measurement channel and said first sensor chamber being otherwise gas-tight;
      a second gas line placing said second sensor chamber in fluid communication with said measurement channel and said second sensor chamber being otherwise gas-tight; and
      a control unit connected to said transducer in said first sensor chamber and to said transducer in said second sensor chamber for operating said transducers to transmit and receive ultrasound therebetween, said ultrasound having a transit time between said transducers, and for measuring said fluid flow dependent on said transit time.

5. A ventilator as claimed in claim 4 further comprising an expiratory line, a measurement tube, and a pressure meter connected to said expiratory line by said measurement tube, for measuring pressure in said expiratory line, and said first gas line and said second gas line being connected to said measurement tube.

* * * * *